United States Patent [19]

Sherts

[11] Patent Number: 5,571,090
[45] Date of Patent: Nov. 5, 1996

[54] VASCULAR SUTURING APPARATUS

[75] Inventor: Charles R. Sherts, Southport, Conn.

[73] Assignee: United States Surgical Corporation, Norwalk, Conn.

[21] Appl. No.: 319,703

[22] Filed: Oct. 7, 1994

[51] Int. Cl.$^6$ .................................................. A61B 17/04
[52] U.S. Cl. .......................... 606/144; 606/139; 606/145
[58] Field of Search ............................ 606/139, 144–148

[56] References Cited

U.S. PATENT DOCUMENTS

| | | |
|---|---|---|
| 1,037,864 | 9/1912 | Carlson et al. . |
| 1,131,163 | 3/1915 | Saunders et al. . |
| 1,293,565 | 2/1919 | Smit . |
| 1,449,087 | 3/1923 | Bugbee . |
| 1,876,792 | 6/1930 | Thompson . |
| 2,213,830 | 9/1940 | Anastasi . |
| 2,880,728 | 4/1959 | Rights . |
| 3,073,311 | 1/1963 | Tibbs et al. . |
| 3,090,386 | 5/1963 | Curtis . |
| 3,349,772 | 10/1967 | Rygg . |
| 3,470,875 | 10/1969 | Johnson . |
| 3,807,407 | 4/1974 | Schweizer . |
| 3,842,840 | 10/1974 | Schweizer . |
| 3,901,244 | 8/1975 | Schweizer . |
| 3,946,740 | 3/1976 | Bassett . |
| 4,021,896 | 5/1977 | Stierlein . |
| 4,109,658 | 12/1978 | Hughes . |
| 4,161,951 | 7/1979 | Scanlan, Jr. . |
| 4,164,225 | 8/1979 | Johnson et al. . |
| 4,236,470 | 12/1980 | Stenson . |
| 4,345,601 | 8/1982 | Fukuda . |
| 4,373,530 | 2/1983 | Kilejian . |
| 4,471,781 | 8/1984 | Di Giovanni et al. . |
| 4,491,135 | 1/1985 | Klein . |
| 4,580,567 | 4/1986 | Schweitzer et al. . |
| 4,621,640 | 8/1986 | Mulhollan et al. . |
| 4,635,638 | 1/1987 | Weintraub et al. . |
| 4,827,931 | 5/1989 | Longmore . |
| 4,890,615 | 1/1990 | Caspari et al. . |

(List continued on next page.)

FOREIGN PATENT DOCUMENTS

| | | |
|---|---|---|
| 0482881 | 4/1992 | European Pat. Off. . |
| 0601676A2 | 6/1994 | European Pat. Off. . |
| 0647431 | 12/1995 | European Pat. Off. . |
| 337579 | 9/1904 | France . |
| 9109097 | 10/1991 | Germany . |
| 4124383C1 | 5/1992 | Germany . |
| 4124381C1 | 8/1992 | Germany . |
| 4127812 | 2/1993 | Germany . |
| 4139628C1 | 3/1993 | Germany . |
| 1103854 | 7/1984 | U.S.S.R. . |
| 1505514 | 9/1989 | U.S.S.R. . |
| 1725847A1 | 4/1992 | U.S.S.R. . |
| 914298 | 1/1963 | United Kingdom . |
| 1249853 | 10/1971 | United Kingdom . |
| 2260704 | 4/1993 | United Kingdom . |
| WO93/01750 | 2/1993 | WIPO . |

OTHER PUBLICATIONS

Machine Design vol. 903, p. 117 (Feb. 28, 1996).
Aesculap Catalog, p. 401 (Date: 1905).

*Primary Examiner*—Gary Jackson

[57] ABSTRACT

There is disclosed an apparatus for suturing vascular tissue sections which includes first and second arms pivotally connected together and each having a needle receiving recess and a needle engaging member mounted for movement within the arms. The apparatus also includes a toggle wheel reciprocating mechanism connected to the first and second needle engaging members and movable for alternately moving the first and second needle engaging members into and out of the first and second needle receiving recesses. The reciprocating mechanism is movable between a first position advancing the first needle engaging member with respect to the first arm and a second position advancing the second needle engaging member with respect to the second arm to alternately secure a surgical needle within the arms. A cam actuating lever is provided on one of the arms to automatically cam the reciprocating mechanism between the first and second positions upon closure of the first arm against the second arm. There is also disclosed a method of suturing a pair of vascular tissue sections utilizing the disclosed apparatus.

22 Claims, 14 Drawing Sheets

U.S. PATENT DOCUMENTS

| | | |
|---|---|---|
| 4,923,461 | 5/1990 | Caspari et al. . |
| 4,935,027 | 6/1990 | Yoon . |
| 4,957,498 | 9/1990 | Caspari et al. . |
| 4,983,176 | 1/1991 | Cushman et al. . |
| 5,059,201 | 10/1991 | Asnis . |
| 5,100,421 | 3/1992 | Christoudias . |
| 5,171,257 | 12/1992 | Ferzli . |
| 5,188,636 | 2/1993 | Fedotov . |
| 5,207,693 | 5/1993 | Phillips . |
| 5,217,471 | 6/1993 | Burkhart . |
| 5,224,948 | 7/1993 | Abe et al. . |
| 5,242,458 | 9/1993 | Bendel et al. . |
| 5,254,126 | 10/1993 | Filipi et al. . |
| 5,261,917 | 11/1993 | Hasson et al. . |
| 5,281,220 | 1/1994 | Blake, III . |
| 5,300,082 | 4/1994 | Sharpe et al. . |
| 5,336,191 | 8/1994 | Davis et al. . |
| 5,389,103 | 2/1995 | Melzer et al. . |
| 5,454,823 | 10/1995 | Richardson et al. . |

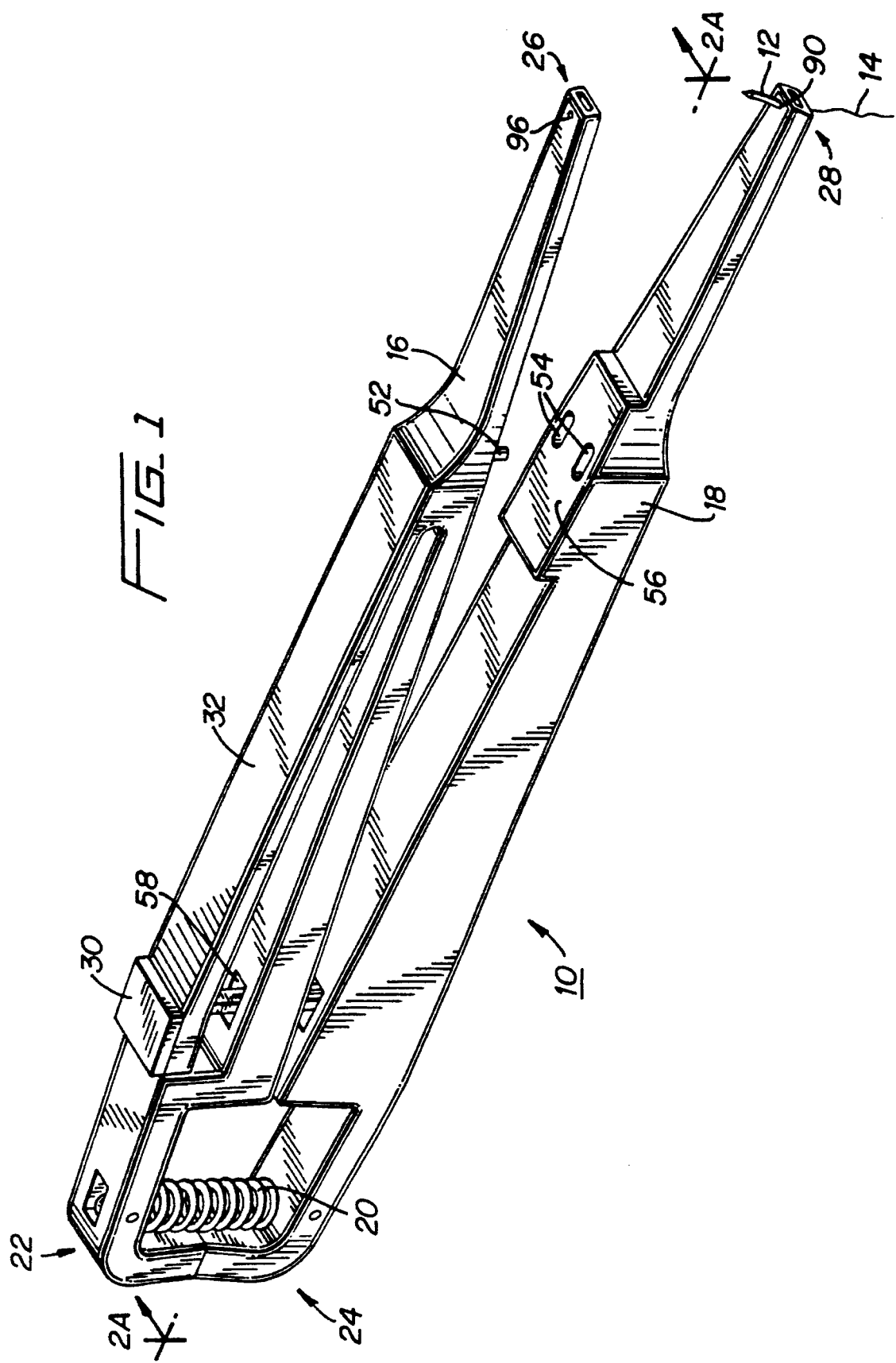

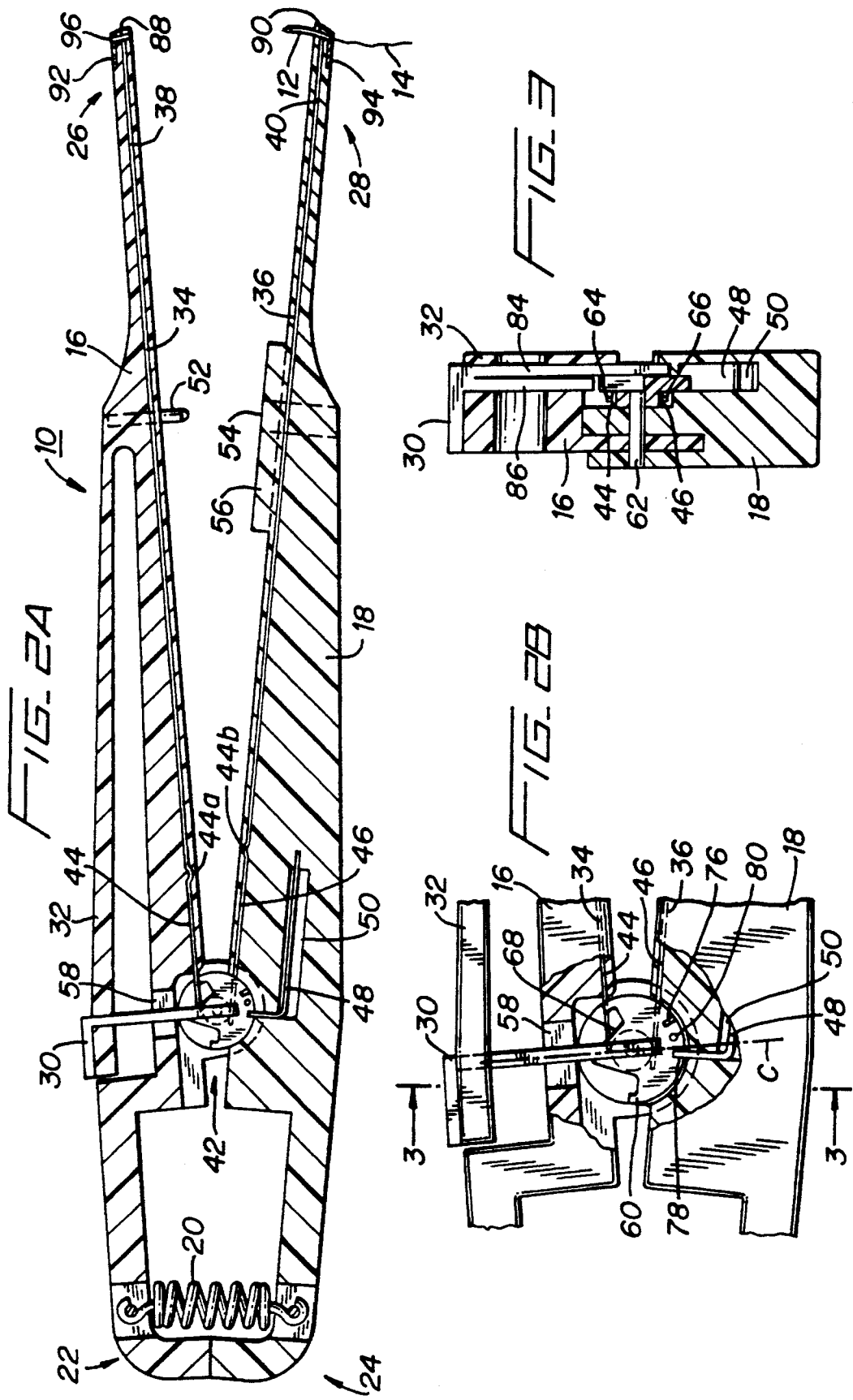

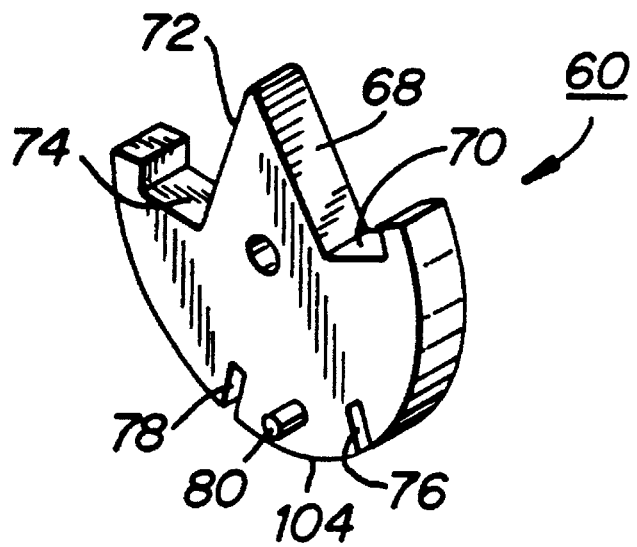
FIG_4
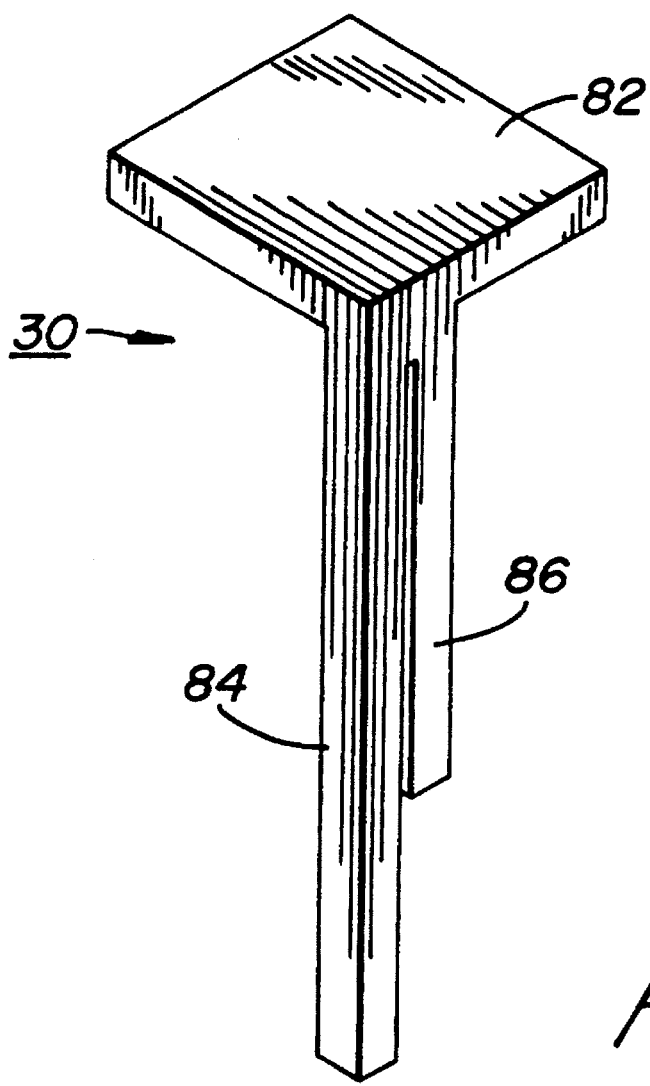
FIG_5

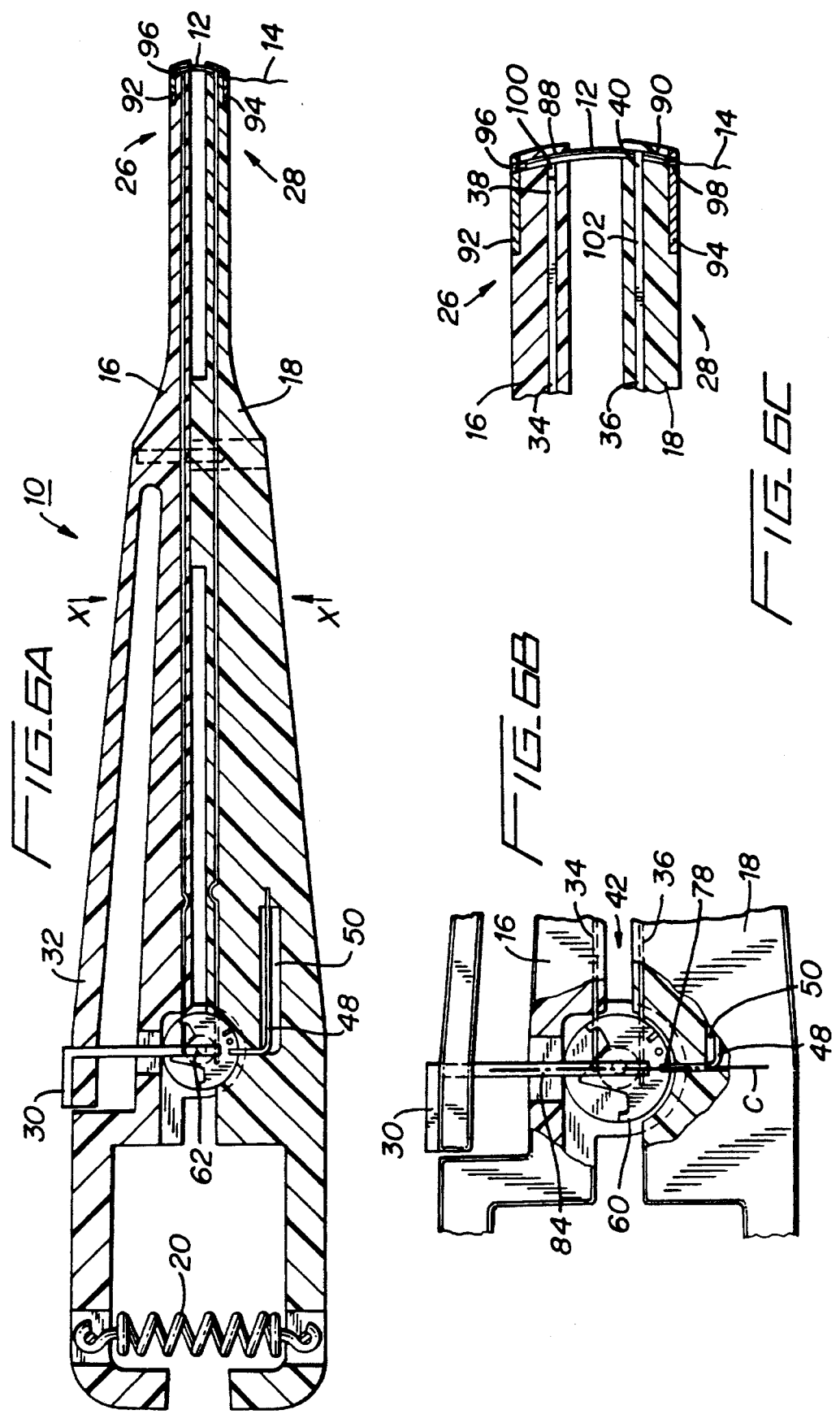

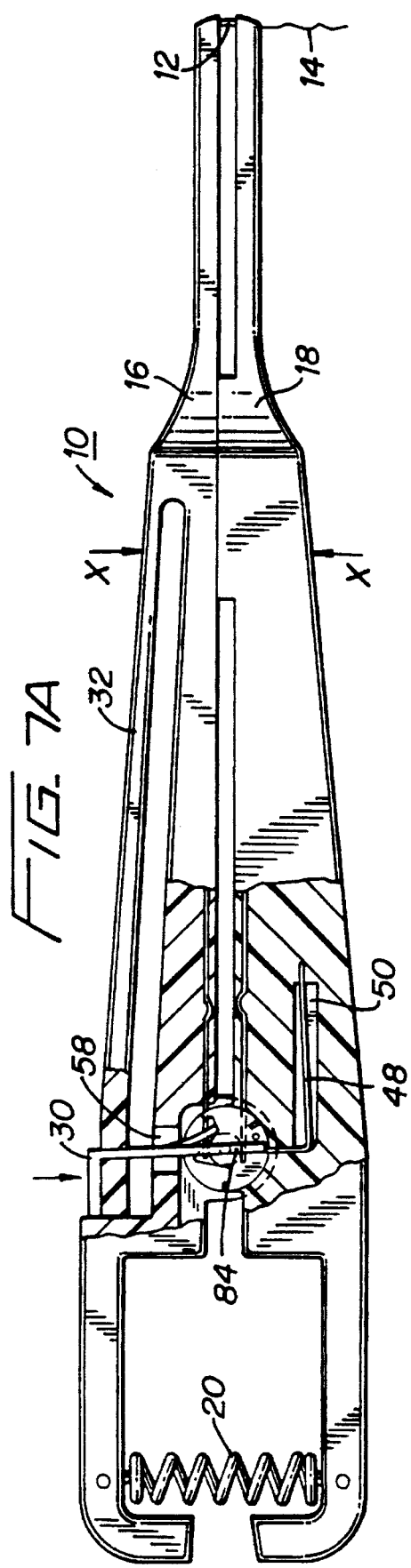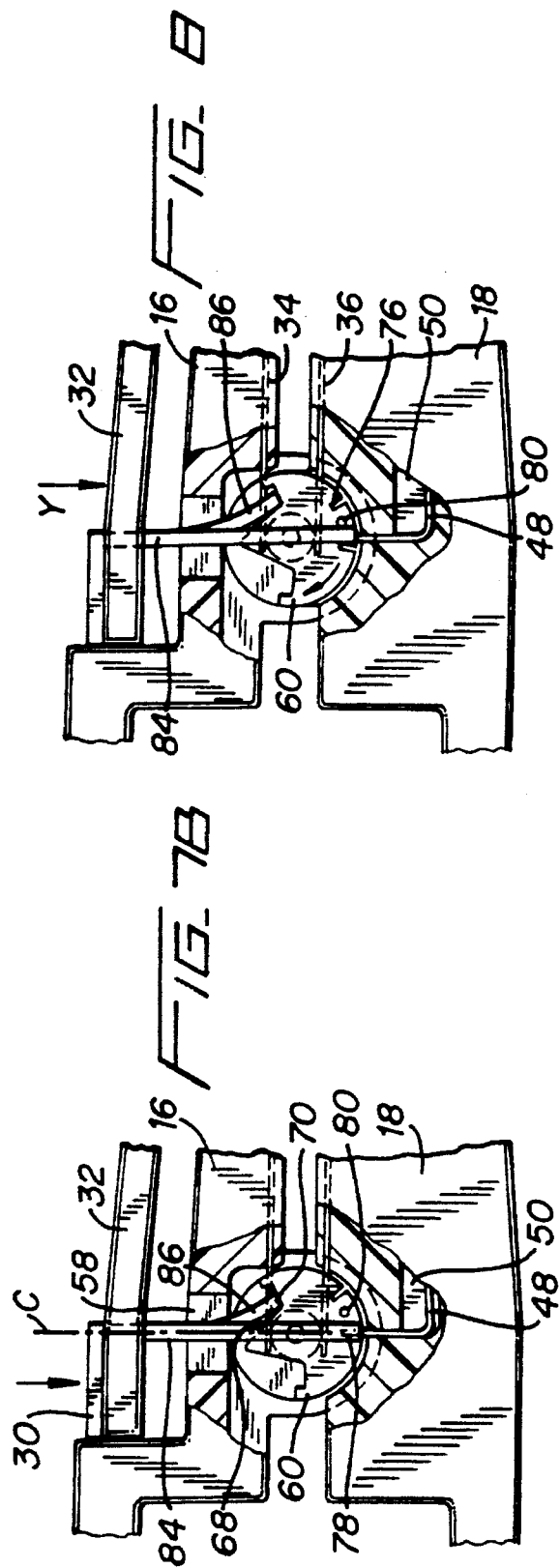

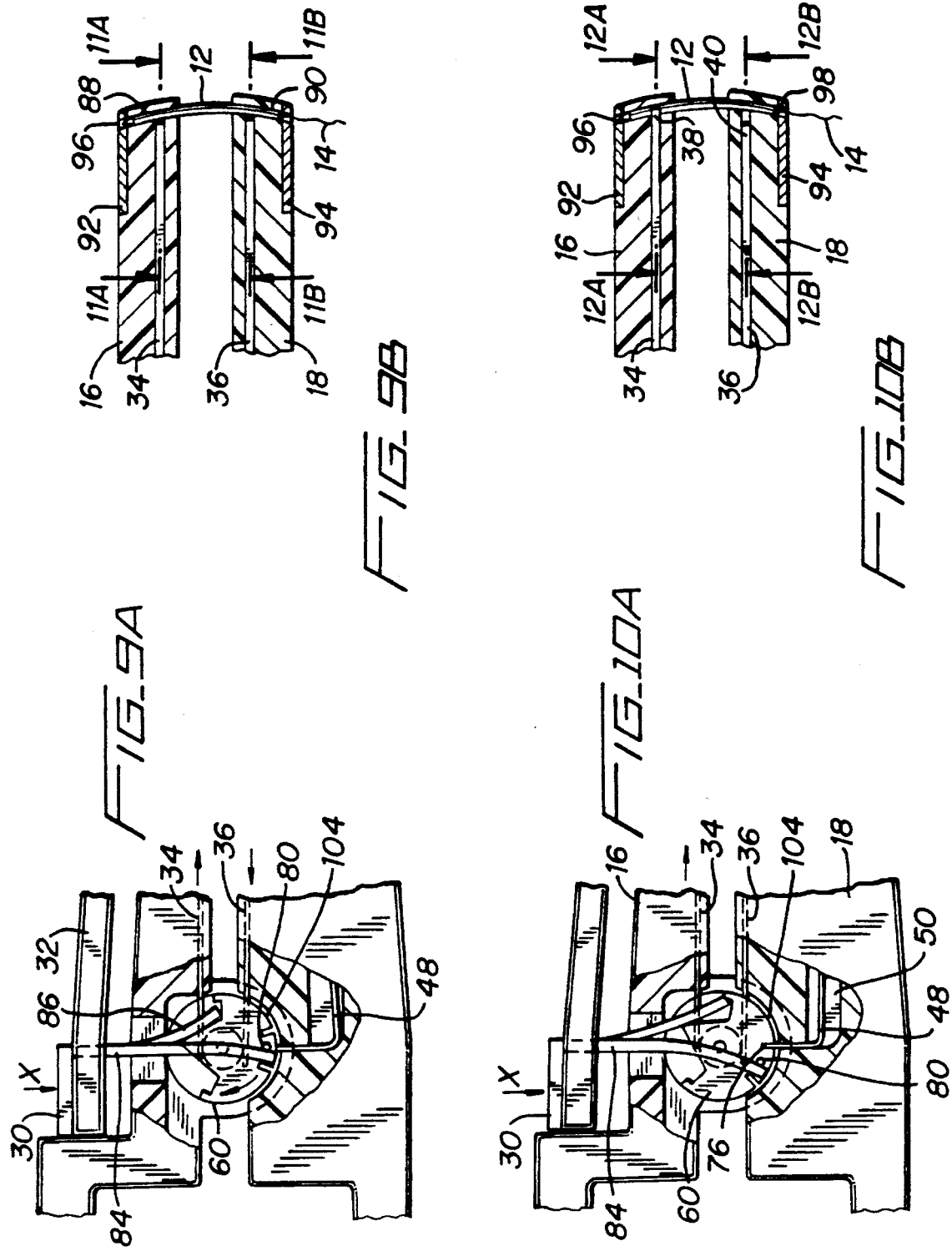

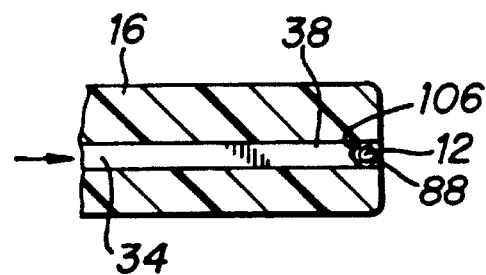
FIG_11A
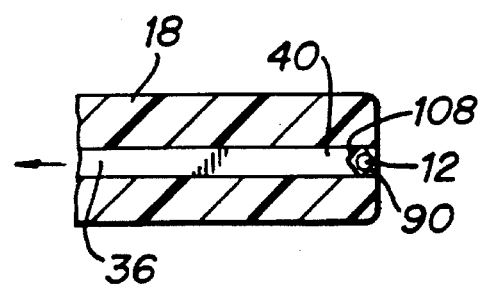
FIG_11B
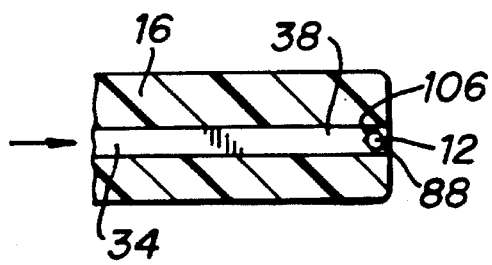
FIG_12A
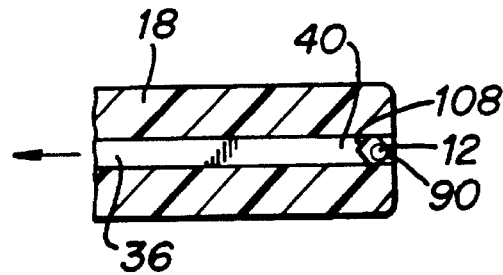
FIG_12B

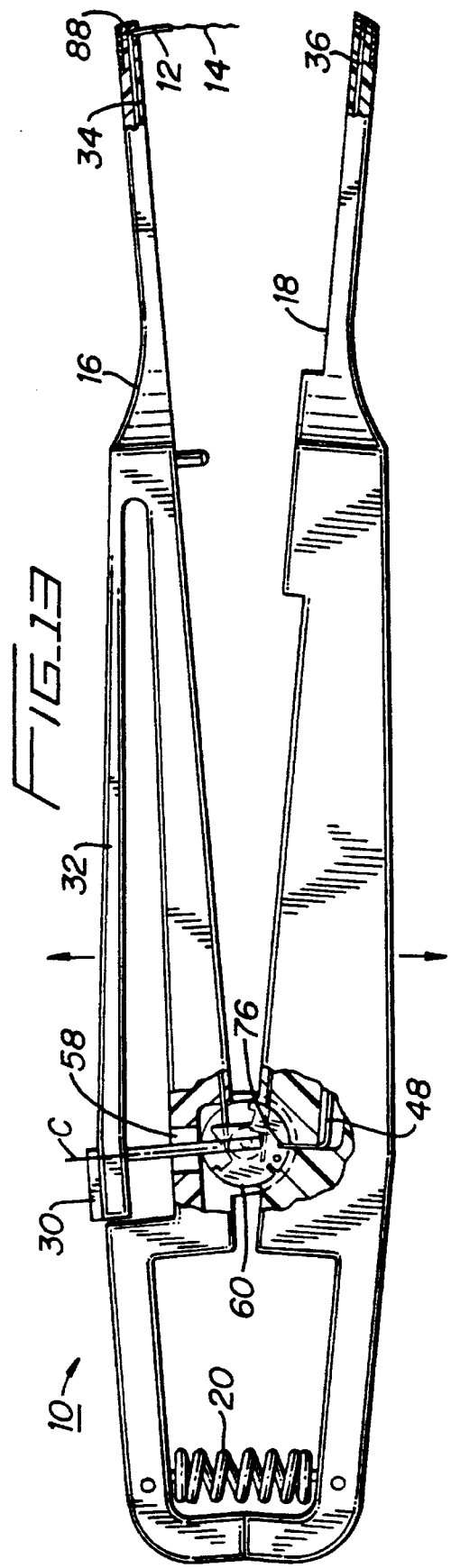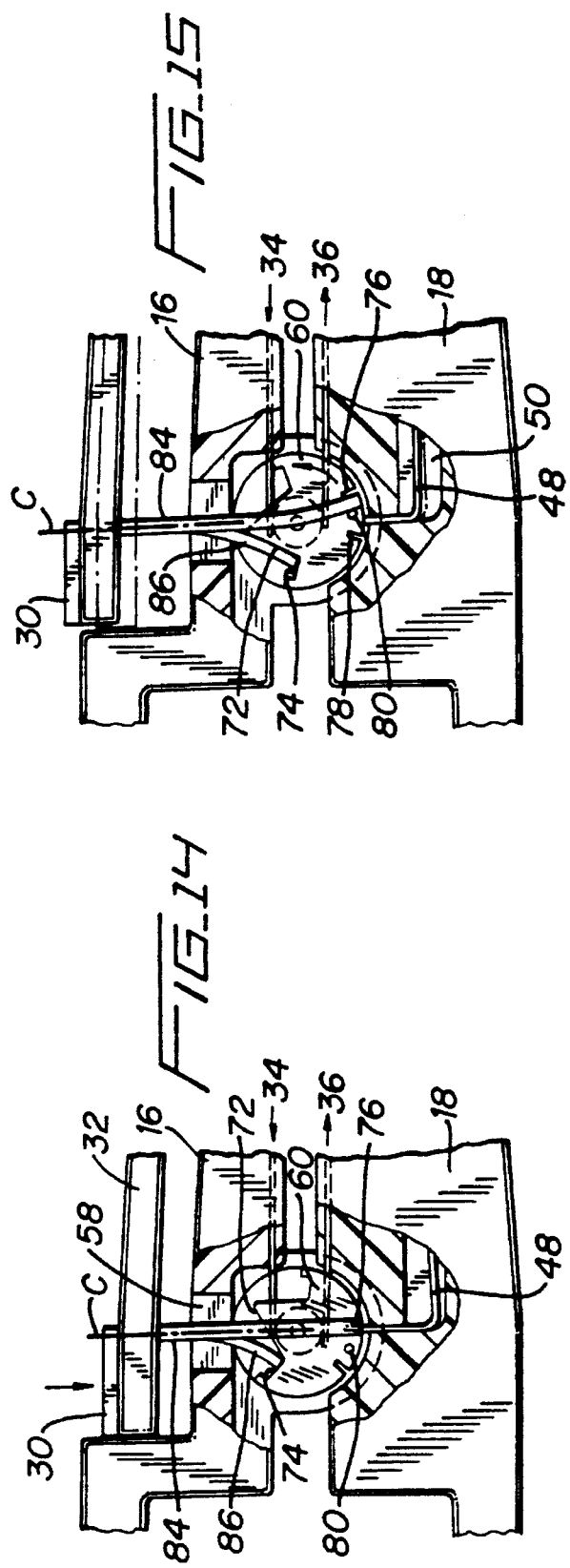

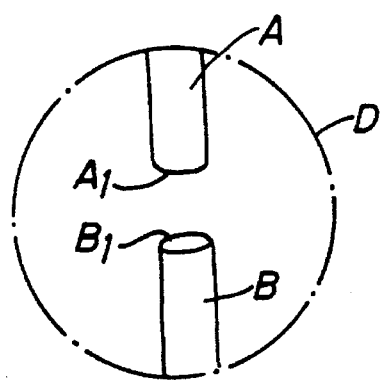
FIG_16A
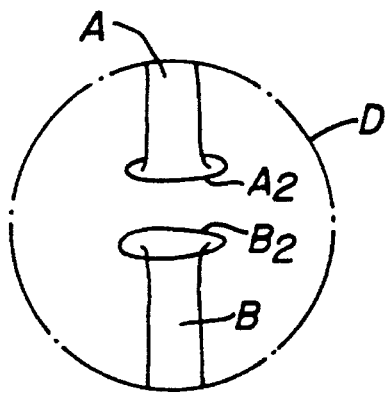
FIG_16B
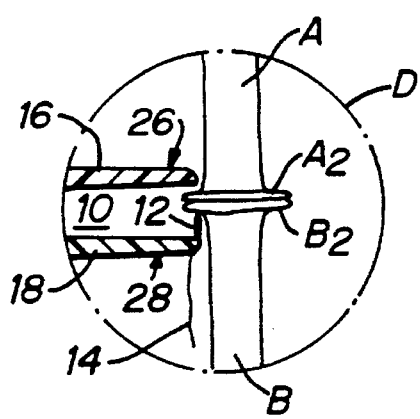
FIG_16C
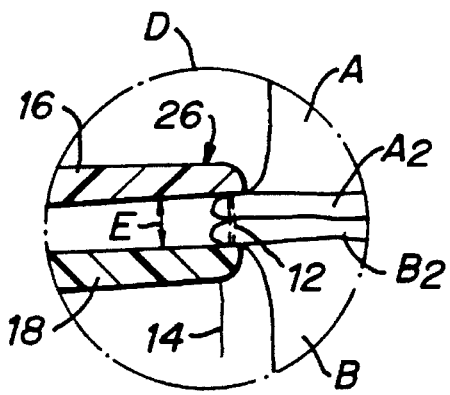
FIG_16D
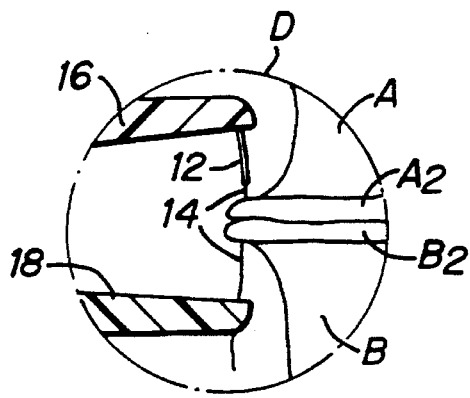
FIG_16E
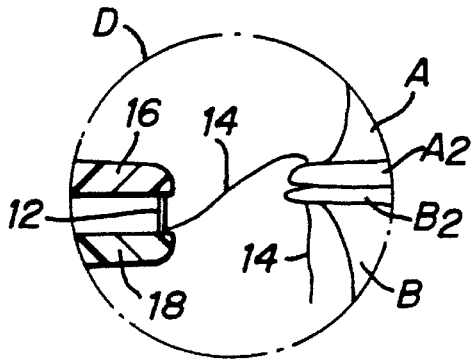
FIG_16F

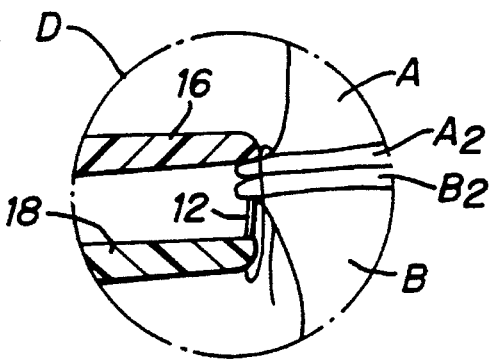
FIG._16G
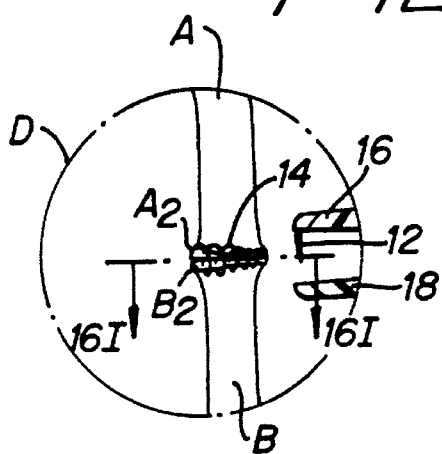
FIG._16H
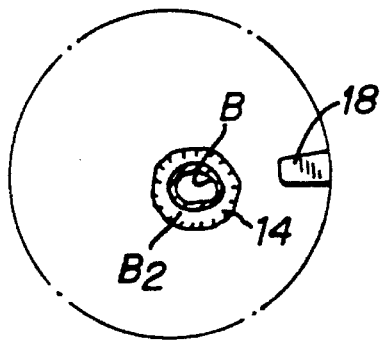
FIG._16I
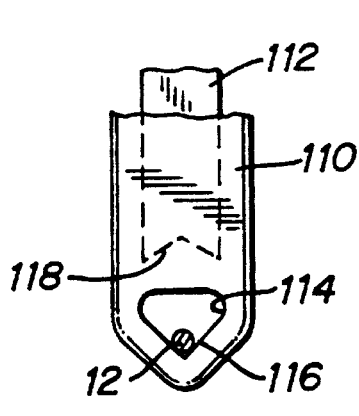
FIG._17A
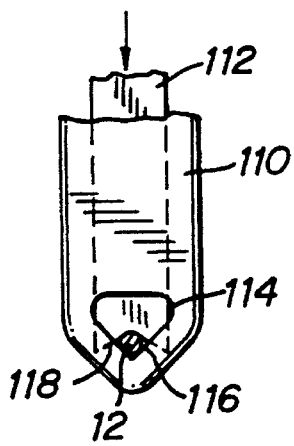
FIG._17B

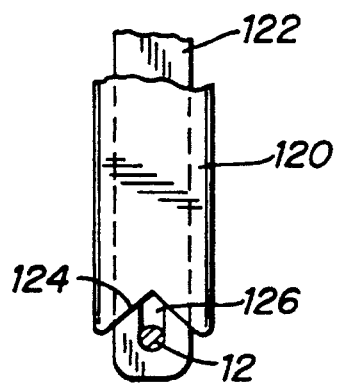
FIG._18A
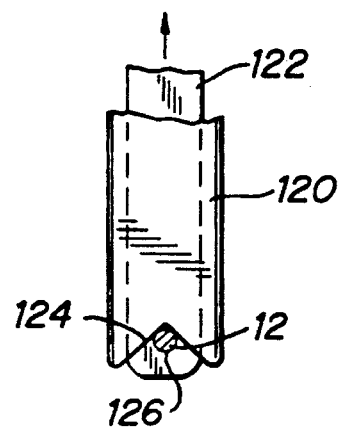
FIG._18B
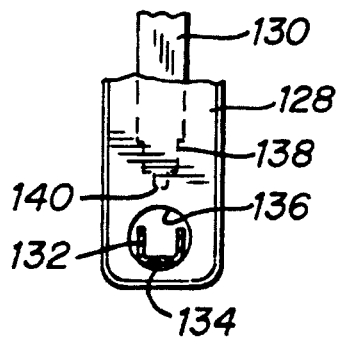
FIG._19A
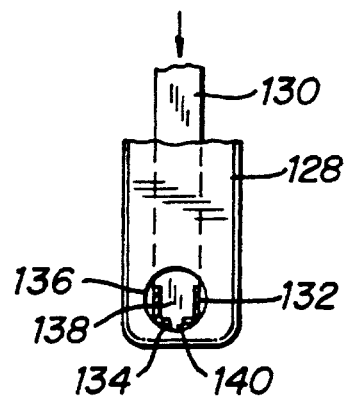
FIG._19B
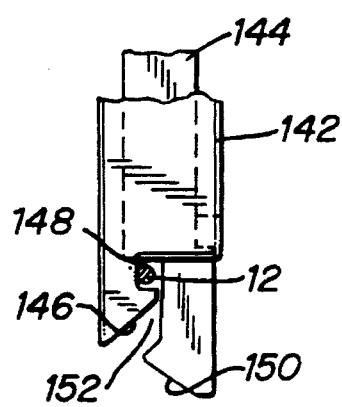
FIG._20A
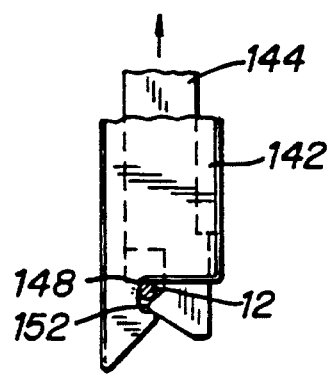
FIG._20B ic Field The technical field relates generally to surgical suturing instrumentation and, more particularly, to a surgical suturing apparatus and a method for suturing vascular tissue sections together.

2. Description of Related Art

During many surgical procedures it is often necessary to join or even rejoin portions of vascular tissues or vessels to form an anastomosis. Various methods of joining vascular tissues to create an anastomosis are used, such as, for example, suturing, stapling or clipping the ends of the vessels together. Additionally, various stents may be used to join the vessels together and create the anastomosis. Where vessels are joined open end to open end it is termed an "end to end" anastomosis. However, in certain surgical procedures it is often desirable to join a free open end of one vessel to an incision in the side of another vessel to create an "end to side" anastomosis or even an incision in the side of another vessel to form "side-to-side" anastomosis.

In some instances suturing of vessels is preferred over stapling or clipping the vessels. Due to the small size of the vessels, a very small suturing needle is used having a length of suture material attached thereto to suture the vessels together. The suturing needle is typically grasped by a needle holder and passed through one vessel and then the opposite vessel. The procedure is repeated to thread or impart a series of stitches to the vessels to suture them together.

Because of the extremely small size of the suturing needle used, typically on the order of ten thousands of an inch in diameter, handling problems may arise while manipulating the suturing needle through the vascular tissues. For example, upon piercing a vessel, the needle must be pushed through the vessel, released by the needle holder at one end of the needle and subsequently grasped at the opposite end of the needle to draw the needle and suture through the vessel thus requiring the release of the needle and suture during the procedure. Release of the needle is often undesirable and may pose problems in regaining control of the needle. To avoid this, it may become necessary to use two needle holders, one positioned on either side of the vessel, to continually grasp the needle, thereby requiring two hands to perform the operation. Additionally, precise control of the needle is often difficult when using typical needle holders. The small size of the needle also makes it difficult and time consuming to recover if dropped during the surgical procedure.

As noted above, the vascular sections to be sutured are typically extremely small. Suturing of such vascular tissue sections is often performed under magnification by equipping the surgeon with special magnifying glasses. The use of these magnifying glasses, while enlarging the view of the vascular tissues and needle, reduces the field of view within which the surgeon has to operate. Thus, as the needle and suture material are passed through the vessels and pulled to draw the suture material through, it often becomes necessary to move the needle holder and needle from the field of view. This may require the surgeon to look away from the field of view containing the vessel sections to be sutured and may present problems in repositioning the needle within the magnified field of view to form another suture in the vascular tissues and increases the time required to suture the vessels together. Even when magnifying glasses are not being used, the surgeon needs to look at the needle as it is moved away from the surgical site to pull the length of suture through the vessel and is passed to his other hand to be re-gripped. Due to the minute size of the vessels, it takes time for the surgeon to refocus on the surgical site to once again pass the needle and suture through the vessel. This repeated change of focus is time consuming and can place a strain on the surgeon's eyes.

Thus, it would be advantageous to have a surgical suturing apparatus and a method of suturing vessels which are particularly suited to suturing vascular tissues in anastomosis procedures. It would further be advantageous to have a surgical suturing apparatus which is operable with a single hand and is capable of maintaining precise and constant control of the needle as it is passed from one needle holding arm of the apparatus to another to avoid release of the needle during the suturing operation. It would also be advantageous to have a surgical suturing apparatus which is capable of suturing vascular tissue sections together with limited hand, apparatus and needle movement in order to maintain the entire suturing operation within a restricted field of view.

SUMMARY

The disclosed surgical apparatus for suturing vascular tissue sections and includes a first arm having a first needle receiving recess and a first needle engaging member or blade mounted for movement with respect to the first arm. A second arm is provided and is mounted for movement with respect to the first arm and has a second needle receiving recess, the second arm having a second needle engaging member or blade mounted for movement with respect to the second arm. There is also provided a reciprocating mechanism connected to the first and second needle engaging members and movable for alternately moving the first and second needle engaging members into and out of the first and second needle receiving recesses to secure a surgical needle therein. The reciprocating mechanism is movable between a first position advancing the first needle engaging member into engagement with the surgical needle and a second position advancing the second needle engaging member into engagement with the surgical needle. A camming member or lever is operatively associated with one of the arms for automatically camming the reciprocating mechanism between the first and second positions upon full closure of the first arm against the second arm.

Preferably, the reciprocating mechanism includes a toggle wheel rotatably affixed the arms and having first and second camming surfaces such that an initial closure of the arms forces the camming member into engagement with the first camming surface to move the toggle wheel to the first position. A subsequent closure of the arms forces the camming member into engagement with the second camming surface to move the toggle wheel to the second position.

There is also disclosed a method of threading a suture through a vascular tissue section which includes the step of providing an apparatus having a first arm with a first needle receiving recess and a second arm with a second needle receiving recess, the first and second arms movable toward and away from each other. The method also includes the steps of holding a surgical needle within the second needle receiving recess, positioning the first and second arms about a first vascular tissue section to be sutured, moving the second arm toward the first arm such that the surgical needle pierces the first vascular tissue section and enters the first needle receiving recess and releasing the surgical needle from the second needle receiving recess and holding the surgical needle within the first needle receiving recess. The method also includes the step of moving the first arm away from the second arm to draw a suture affixed to the surgical needle at least partially through the first vascular tissue section.

BRIEF DESCRIPTION OF THE DRAWINGS

Various embodiments are described herein with reference to the drawings, wherein:

FIG. 1 is a perspective view of a vascular surgical suturing apparatus with arms in an open position and holding a surgical suturing needle within one of the arms;

FIG. 2A is a side cross-sectional view of the suturing apparatus taken along line 2A—2A of FIG. 1;

FIG. 2B is an enlarged side view, partially shown in section, depicting the reciprocating mechanism of the suturing apparatus of FIG. 1;

FIG. 3 is a cross-sectional view taken along line 3—3 of FIG. 2B;

FIG. 4 is a perspective view of the toggle wheel;

FIG. 5 is a perspective view of the camming lever for moving the toggle wheel;

FIG. 6A is a side cross-sectional view similar to FIG. 2A depicting the arms moved to a closed position;

FIG. 6B is an enlarged side view, partially shown in section, of the reciprocating mechanism position corresponding to the position of FIG. 6A;

FIG. 6C is an enlarged side cross-sectional view of the distal end of the suturing apparatus corresponding to the position of 6A;

FIG. 7A is a side view of the vascular surgical suturing apparatus of FIG. 1, partially shown in section, illustrating initial actuation of the reciprocating mechanism in a clockwise direction;

FIG. 7B is an enlarged side view, partially shown in section, of the reciprocating mechanism position corresponding to the position of FIG. 7A;

FIG. 8 is a view similar to FIG. 7B, illustrating further actuation of the reciprocating mechanism;

FIG. 9A is a view similar to FIG. 8, illustrating still further actuation of the reciprocating mechanism;

FIG. 9B is an enlarged side cross-sectional view of the distal end of the suturing apparatus of FIG. 1 corresponding to the reciprocating mechanism position of FIG. 9A;

FIG. 10A is a view similar to FIG. 9A, illustrating a final position of the reciprocating mechanism;

FIG. 10B is a view similar to FIG. 9B corresponding to the position of FIG. 10A;

FIG. 11A is a cross-sectional view taken along the line 11A—11A of FIG. 9B;

FIG. 11B is a cross-sectional view taken along the line 11B—11B of FIG. 9B;

FIG. 12A is a cross-sectional view taken along the lines 12A—12A of FIG. 10B;

FIG. 12B is a cross-sectional view taken along the lines 12B—12B of FIG. 10B;

FIG. 13 is a side view of the vascular surgical suturing apparatus, partially shown in section, illustrating the surgical needle positioned in the opposing arm;

FIG. 14 is an enlarged side view, partially shown in section, of the reciprocating mechanism illustrating initial actuation of the reciprocating mechanism in an opposite (counterclockwise) direction;

FIG. 15 is a view similar to FIG. 14, illustrating further actuation of the reciprocating mechanism;

FIG. 16A is a perspective view of a pair of vascular tissue sections to be end to end sutured as viewed within a limited field of view under magnification;

FIG. 16B is a view similar to FIG. 16A with the ends of the vessels everted in preparation for suturing;

FIG. 16C is a sectional view of a distal end of the surgical suturing apparatus of FIG. 1 and the pair of everted vessels ready for suturing;

FIG. 16D is a view similar to FIG. 16C illustrating the piercing of the everted edges of the vascular sections by the surgical needle;

FIG. 16E is a view similar to FIG. 16D illustrating the surgical needle having been passed to an opposing arm and the suture being drawn through the everted vessel edges;

FIG. 16F is a view similar to view 16E illustrating the surgical needle being passed back to the first arm.

FIG. 16G is a view similar to FIG. 16D illustrating the arms being closed again about the everted vessel ends to pierce the vessels and form another stitch;

FIG. 16H is a view of the vessels sutured together to form an end to end anastomosis;

FIG. 16I is a view taken along lines I—I of FIG. 16H;

FIGS. 17A and 17B are enlarged views of an alternate suturing apparatus distal end and associated needle engaging member configuration;

FIGS. 18A and 18B are enlarged views of another alternate distal end and needle engaging member configuration;

FIGS. 19A and 19B are enlarged views of a further alternate distal end and needle engaging member configuration for use with a suturing needle having a hole at least partially therethrough;

FIGS. 20A and 20B are enlarged views of yet another alternate distal end and needle engaging member arrangement;

DESCRIPTION OF PREFERRED EMBODIMENTS

Figure 19C:
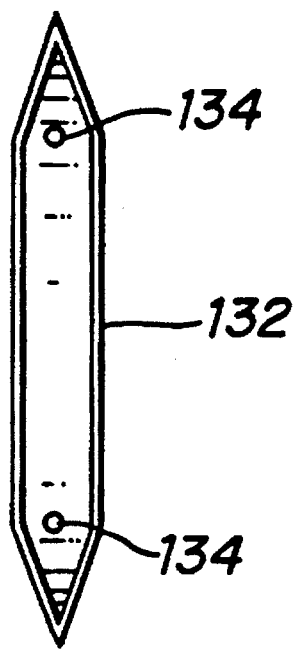
FIG. 19C is a side plan view of a double pointed suturing needle having a hole at least partially therethrough.

Referring to FIG. 1, there is depicted a vascular suturing apparatus 10 which is particularly suited to facilitate suturing vascular tissue sections or vessels together. Further, apparatus 10 is specifically designed to repeatedly pass a small surgical needle, having an associated length of suture material attached thereto, such as, for example, surgical needle 12 and suture 14, through vascular tissue sections while maintaining precise control of needle 12 during all phases of the suturing operation.

Apparatus 10 generally includes a first or upper arm 16 movably connected to a second or lower arm 18. Arms 16 and 18 are movable toward and away from each other in order to repeatedly pass needle 12 therebetween in a manner described in detail hereinbelow. Preferably, apparatus 10 is approximately 7 inches long. Apparatus 10 is preferably designed to handle surgical needles 12 having a length of approximately 0.1 to 0.5 inches and a diameter of approximately ten thousandths to 0.025 of an inch which are particularly suited for vascular surgery. Preferably the diameter of the surgical needle and the diameter of the suture are substantially the same to prevent fluid leakage from the vessel between the needle hole and suture.

Note that the use of the terms "upper" and "lower" herein refers to the orientation of the instrument in FIG. 1. Clearly, if the orientation changes, these designations will likewise change.

In many instances, certain ergonomic and operational advantages may be obtained by biasing a surgical suturing instrument in an initially open position. Thus, in this embodiment there is provided a spring 20 which is affixed to proximal ends 22 and 24 of first and second (or upper and lower in the orientation of FIG. 1) arms 16 and 18, respectively. Spring 20 biases apart distal ends 26 and 28 of first and second arms 16 and 18, respectively, in order to facilitate positioning arms 16 and 18 about vascular tissue sections. The biasing action of spring 20 also aids in pulling suture 14 through the tissue sections upon opening of arms 16 and 18.

Apparatus 10 further includes holding structure to secure needle 12 within either distal end 26 and 28 of arms 16 and 18, respectively. The holding structure allows surgical needle 12 lo to be initially held within one of the arms and, upon closure of the arms, to be subsequently passed to the opposite arm. To facilitate single handed use of apparatus 10, a cam actuating lever 30 is provided to automatically actuate the holding structure upon closure of the arms. Cam actuating lever 30 is affixed to an extension arm 32 formed on arm 16. Extension arm 32 is sufficiently stiff to prevent depression of cam actuating lever 30 before arms 16 and 18 have been closed against the bias of spring 20. Thus, after such closure of arms 16 and 18, continued pressure on arms 16 and 18 depresses cam actuating lever 30 to automatically actuate the holding structure to release the surgical needle 12 from one arm for transfer to an opposite arm as described in more detail hereinbelow.

Referring now to FIG. 2A, in order to hold or secure needle 12 within arms 16 or 18, there are provided a pair of needle engaging members or clamping blades 34, 36 which are longitudinally movable within arms 16 and 18. A first needle engaging blade 34 is slidably disposed within first arm 16 while a second needle engaging member or second blade 36 is slidably disposed within second arm 18. Distal ends 38 and 40 of first and second blades 34 and 36, respectively, are dimensioned and configured to engage an edge of needle 12 and securely hold needle 12 within recesses 88, 90 formed in first and second arms 16 and 18. To prevent damage to a tip or needle point of surgical needle 12 and to prevent the suture carrying end from sliding through arm 18, there are provided a pair of plates 92 and 94 formed in distal ends 26 and 28, respectively, each of which include a reduced recess area 96 and 98 to prevent surgical needle 12 from sliding completely through recesses 88 and 90 in arms 16 and 18, respectively. Arms 16 and 18 are formed with longitudinally extending channels 100 and 102 which extend from distal ends 38 and 40 to reciprocating mechanism 42. Channels 100 and 102 intersect recesses 88 and 90 to allow members 34 and 36 to engage an edge of surgical needle 12 disposed in the respective recess.

As shown in FIG. 2A, needle engaging members 44, 46 are slightly bowed at regions 44a, 44b, respectively, thereby automatically adjusting to needles of various diameters. That is, as the needle is clamped, the needle engaging member buckles at a predetermined location so that the spring force applied to the needle is constant, regardless of the needle diameter. The needle engaging member is slightly buckled even when the needle is not clamped to ensure that the increased buckling occurs in the same area whenever the needle is clamped.

While the preferred blade engagement structure includes V-notches 106 and 108, it will be appreciated by those skilled in the art the various other configurations at blade distal ends 38 and 40 may be provided to securely hold needle 12 within arms 16 and 18. Thus, alternate structure in either arms 16 or 18 or alternate structure in needle 12 itself such as, for example, notches in an edge of needle 12, or holes completely therethrough, may be provided to accept corresponding engagement structure formed on blades 34 and 36. Thus, for example, a double-pointed surgical needle, or surgical incision member, having suture attachment structure intermediate the points may be utilized. One exemplary example of a surgical incision member is disclosed in U.S. patent application Ser. No. 08/260,579, filed Jun. 16, 1994, and entitled SURGICAL INCISION MEMBER the disclosure of which is incorporated by reference herein.

To repeatedly pass needle 12 between arms 16 and 18, a reciprocating mechanism 42 is affixed adjacent proximal ends 44 and 46 of first and second engaging members 34 and 36, respectively. Reciprocating mechanism 42 alternately advances and retracts engaging members 34 and 36, within arms 16 and 18, respectively, thereby alternately engaging the members 34 and 36 with needle 12. Reciprocating mechanism 42, along with first and second engaging members 34 and 36, provide the aforementioned holding structure for securely and alternately holding needle 12 within needle receiving recesses formed in arms 16 and 18.

Cam actuating lever 30 actuates reciprocating mechanism 42 automatically upon full closure of arms 16 and 18. In order to prevent inadvertent release of surgical needle from arms 16 or 18 prior to closure of arms 16 and 18, there is provided a lock member 48 which is flexibly mounted within a recess 50 in lower arm 18. Lock member 48 is engagable with reciprocating mechanism 42 to prevent movement of reciprocating mechanism 42, and thus release of needle 12, when arms 16 and 18 are in a open position, i.e., when cam actuating lever 30 has not been depressed.

As noted hereinabove, apparatus 10 is particularly suited to suturing small vessels or vascular tissue sections when viewed under magnification or within a restricted field of view. Further, suturing of vessels requires an extremely small needle 12 and suture 14, typically on the order of ten thousands of an inch in diameter. Thus, in order to ensure precise positioning and transfer of needle 12 between arms 16 and 18 upon closure there are provided a pair of alignment pins 52 which are mounted on first arm 16. Upon closure of arm 16 towards arm 18, alignment pins 52 enter into guide holes 54 formed in lower arm 18. The engagement of alignment pins 52 within guide holes 54 is sufficiently precise to ensure accurate alignment of needle 12 within the recesses 88, 90 formed in distal ends 26 and 28 of arms 16 and 18, respectively. Additionally, to prevent the vascular tissue sections from being compressed or crushed during the suturing operation, there is provided a spacer block 56 which ensures that distal ends 26 and 28 of arms 16 and 18, respectively, do not touch upon closure. However, spacer block 56 does allow arms 16 and 18 to close sufficiently such that needle 12 may be transferred therebetween.

Referring now to FIG. 2B, actuation of the reciprocating mechanism 42, is caused by cam actuating lever 30 extending through an aperture 58 formed in arm 16. Reciprocating mechanism 42 preferably includes a rotatable toggle wheel 60 which is provided to alternately advance or retract needle engaging members 34 and 36 in response to depression of cam actuating lever 30 upon full closure of arms 16 and 18, i.e. in response to movement of extension arm 32 with respect to arm 16. Toggle wheel 60 additionally provides recesses (described below) for engagement with lock member 48.

As noted hereinabove, first and second arms 16 and 18 are movably connected together and configured to be operated in a tweezer-like manner if desired. Referring to FIG. 3, arms 16 and 18 are provided with a transverse pivot pin 62 for connecting and pivotally moving arms 16 and 18 with respect to each other. Pivot pin 62 is connected to arms 16 and 18 at a position intermediate proximal ends 22, 24 and distal end 26, 28 of arms 16 and 18, respectively. Thus, pressure on arms 16 and 18 distally of pivot pin 62, to close distal ends 26, 28, stretches spring 20, while release of arms 16 and 18 allows spring 20 to bias distal ends 26 and 28 to an open or spaced apart position.

While the preferred position of pivot pin 62, and thus the pivot point of arm 16 and 18, is intermediate the ends of apparatus 10, pivot pin 62 may be positioned at proximal ends 22 and 24. Further, although the preferred method of moving arms 16 and 18 is by pivotal motion, parallel movement of arms 16 and 18 is also contemplated. Parallel movement of arms 16 and 18 is especially desirable when using relatively straight surgical needles and may be accomplished in several ways. For example, arms 16 and 18 could be mounted with respect to each other to both move perpendicular to their respective longitudinal axes. Alternately, arms 16 and 18 could be mounted to move or slide parallel to their respective longitudinal axes to advance and retract their distal ends. When arms 16 and 18 slide relative to each other, it is preferable to have the distal faces of the arms open to a needle holding recess to facilitate transfer of a surgical needle or surgical incision member therebetween.

Pin 62 further serves as a pivot point for toggle wheel 16 which is rotatable in the clockwise or counterclockwise direction about pin 62. Preferably, proximal ends 44 and 46 of needle engaging members 34 and 36, respectively, are affixed to toggle wheel 60 by means of pins 64 and 66, respectively (see FIG. 3). Thus, rotation of toggle wheel 60 on pivot pin 62 alternately advances and retracts members 34 and 36 within arms 16 and 18, respectively.

Referring to FIGS. 2A and 4, toggle wheel 60 is provided with a first angled camming surface 68 having a first ledge 70 which, when engaged by cam actuating lever 30, translates to a clockwise rotation of toggle wheel 60 and thus a distal advancement of needle engaging member 34 and a proximal retraction of needle engaging member 36. Similarly, a second angled camming surface 72 and second ledge 74 are provided, such that when engaged by cam actuating lever 30, toggle wheel 60 is rotated in a counterclockwise direction to advance member 36 and retract member 34.

Toggle wheel 60 is provided with lock notches 76 and 78 which correspond to the distalmost advancement of first and second needle engaging members 34 and 36, respectively. Thus, when toggle wheel 60 is rotated counterclockwise to a position where lock member 48 engages lock notch 78, engaging member 36 is locked into an advanced or distalmost position to securely hold needle 12 within arm 18. Likewise, when toggle wheel 60 is rotated clockwise to a position where lock member 48 engages lock notch 76, needle engaging member 34 is locked into an advanced or distalmost position to secure needle 12 within arm 16. Thus, lock member 48, in conjunction with lock notches 76 and 78, prevents release and transfer of needle 12 when arms 16 and 18 are not fully closed. Additionally, toggle wheel 60 is provided with a knock off pin 80 to aid lock member 48 in entering lock notches 76 and 78, the operation of which is described in more detail hereinbelow.

Referring now to FIGS. 2B and 5, cam actuating lever 30 is provided to automatically perform the dual sequential functions of unlocking toggle wheel 60 from engagement with lock member 48 and rotating toggle wheel 60. Cam actuating lever 30 generally includes a base portion 82 which is preferably affixed to arm extension member 32. Alternatively in a non-automatic version, base 82 may be separately movable with respect to extension member 32. Cam actuating lever 30 includes a flexible release leg 84 which is affixed to base 82 and which is provided to cam lock member 48 out of lock notchs 76 or 78 and thus allow toggle wheel 60 to be rotated. Cam actuating lever 30 also includes a flexible toggle leg 86 formed parallel to release leg 84. Toggle leg 86 is engagable with angled camming surfaces 68 and 72 and ledges 70 and 4 in order to rotate toggle wheel 60.

Referring initially to FIGS. 1 and 2A, the operation of vascular suturing apparatus 10 will now be described. As noted hereinabove, apparatus 10 is particularly suited to repeatedly pass surgical needle 12 back and forth between arms 16, 18 automatically upon full closure of the arms, i.e. closure of arms 16 and 18 with respect to one another and subsequent closure of arm extension 32 with respect to arm 16. In the initial position, distal ends 26 and 28 of arms 16 and 18, respectively, are biased to an open position by spring 20. Needle 12, having an associated length of suture material 14 attached thereto, is positioned and held within distal end 28 of second (lower) arm 18 by needle engaging member 36. Alignment pins 52 are spaced from guide holes 54 and extension arm 32 is in an unbiased state holding camming lever 30 away from toggle wheel 60 in the initial position. To facilitate transfer of needle 12 between arms 16 and 18, needle 12 preferably has a radius of curvature which is substantially equal to the distance between either needle recess, described hereinbelow, and the pivot point, i.e., pin 62, of apparatus 10. In this manner the radius of curvature of surgical needle 12 matches the arc defined by the closure of arms 16 and 18.

Referring now to FIG. 2B, still in the initial position, toggle wheel 60 is in a counterclockwise most position with lock member 48 in engagement with lock notch 78 of toggle wheel 60 to prevent rotation. Thus, surgical needle 12 is locked into second (lower) arm 18. It will be noted that a portion of angled camming surface 68 of toggle 60 is oriented at a position slightly proximal of a center line c of cam actuating lever 30, and, as best shown in FIG. 3, toggle leg 86 is spaced above toggle wheel 60 while release leg 84 is spaced above lock member 48. When arms 16 and 18 are in an open position, center line c, and thus release leg 84, are not in alignment with lock member 48. Thus any inadvertent depression of cam actuating lever 30 prior to closure of arms 16 and 18 will not result in release of lock member 48 from lock notch 78.

Referring now to FIG. 6A, to actuate vascular suturing apparatus 10, pressure is applied to first and second arms 16 and 18 at a point distal of pivot pin 62 in the direction of arrows X to cause jaws 16 and 18 to come to a closed position where distal ends 26 and 28 are in close cooperative alignment. Arms 16 and 18 are closed against the bias of spring 20 which now assumes a stressed state. As best shown in FIG. 6B, upon closure of arms 16 and 18, the center line C of cam actuating lever 30 and thus of release leg 84 is rotated into alignment above lock member 48. Note at this point, due to the relative stiffness of extension arm 32, arm 32 has not moved in relation to arm 16.

Referring to FIGS. 6B and 6C, when toggle wheel 60 is in a counterclockwise most rotation with lock member 48 engaging lock notch 78, (corresponding to needle 12 held in the upper arm 16 as viewed in the orientation of FIG. 6C), needle engaging blade 36 is in a distally advanced position such that distal end 40 of member 36 engages an edge of surgical needle 12. Engaging member 34 of lower arm 14 is in a proximalmost position with its distal end 38 disengaged from surgical needle 12.

Referring now to FIG. 7A, continued depression on arm extension 32 of upper arm 16 causes arm extension 32 to move because arms 16 and 18 are in abutment. This movement of arm extension 32 moves cam actuating lever 30 attached thereto through aperture 58. As cam actuating lever 30 is moved downwardly through aperture 58, release lever 84 contacts lock member 48 to move it downwardly and out of engagement with lock notch 78 (see FIG. 7B). Thus, toggle wheel 60 is released for rotation. After lock member 48 has been disengaged from lock notch 78, cam actuating lever 30 performs its second function as toggle lever 86 of lever 30 contacts camming surface 68 and ledge 70 of toggle wheel 60 to initiate rotation in a clockwise direction. As noted hereinabove, toggle lever 86 will engage angled camming surface 68 due to the positioning of a portion of angled camming surface 68 slightly proximal of a center line C of cam actuating lever 30.

Further pressure on extension member 32 as shown by arrow Y in FIG. 8 causes toggle lever 86 to further rotate toggle wheel 60 in a clockwise direction. Clockwise rotation of toggle wheel 60 begins to advance upper needle engaging member 34 in a distal direction and retract lower needle engaging member 36 in a proximal direction.

Note that when cam actuating lever 30 is depressed release leg 84 moves lock member 48 out of lock notch 78, and holds it down and away from toggle wheel 60. To allow lock member 48 to spring back up and into engagement with lock notch 76 upon complete rotation of toggle wheel 60, knock off pin 80 is provided to move flexible release leg 84 away from lock member 48. Thus, as shown, when toggle wheel 60 is rotated in a clockwise direction, knock off pin 80 moves into abutment with a lower end of release leg 84.

As cam actuating lever 30 is continuingly depressed (by movement of arm extension 32), with reference to FIG. 9A, toggle leg 86 rotates toggle wheel 60 in a clockwise direction thereby causing knock off pin 80 to move release leg 84 away from and off of lock member 48. Thus as toggle wheel 60 is rotated, lock member 48 now rides along, and is held down by, a lower circumferential surface 104 of toggle wheel 60. Needle engaging members 34 and 36 continue to be advanced and retracted respectively. Referring to FIG. 9B, and as noted above, when jaws 16 and 18 are in a closed position, surgical needle 12 is held within recesses 88 and 90 in distal ends 26 and 28, respectively. Plates 92 and 94 having reduced recess areas 96, 98 prevent surgical needle 12 from sliding out of recesses 88 and 90. Thus upon rotation of toggle wheel 60 to cause member 34 to advance and member 36 to retract, surgical needle 12 is securely contained within jaws 16 and 18 although neither of the needle engaging members 34 are in engagement with surgical needle 12. This non-engagement of the needle engaging members 34, 36 is illustrated in FIGS. 11A and 11B as the V-shaped camming edges 106, 108, respectively are out of contact with surgical needle 12.

Referring to FIG. 10A, it can be seen that further depression of arm extension 32 and attached cam actuating lever 30 results in toggle wheel 60 rotating to a fully clockwise or final position. As noted above, release lever 84 is held out of alignment with lock member 48 by means of knock off pin 80. Thus, as toggle wheel 60 is rotated to the final position, lock notch 76 assumes a position directly above lock member 48 and lock member 48, being spring biased, moves upward within recess 50 to engage lock notch 76. Thus, toggle wheel 60 becomes locked out from further rotation. Any further depression of cam actuating lever 30 at this time will cause no further rotation of toggle wheel 60.

In FIG. 10B toggle wheel 60 is in a clockwise position, upper needle engaging member 34 is in a distalmost position while lower needle engaging member 36 is in a proximalmost position. Thus, distal end 38 of needle engaging member 34 engages an edge of surgical needle 12 while distal end 40 of member 36 remains disassociated from surgical needle 12. This is shown in FIGS. 12A and 12B where V-shaped camming edge 106 of needle engaging member 34 cams or wedges surgical needle 12 within respective recess 88 and V-shaped camming edge 108 of needle engaging member 36 is moved to its proximalmost position spaced from surgical needle 12.

Thus, in this manner, surgical needle 12 has been transferred from arm 18 to arm 16 while containing needle 12 within recesses 88 and 90, thereby accomplishing the transfer of needle 12 from arms 18 to 16 without risk of release or escape of needle 12.

As shown in FIG. 13, pressure is then released from arms 16 and 18, resulting in spring 20 biasing arms 16 and 18 into an open position. Arms 84 and 86 of lever 30 also spring back to their starting positions. Needle engaging member 36 is disengaged from surgical needle 12 while member 34 is engaged and securely holds surgical needle 12 within recess 88 in arm 16. Lock member 48 engagement with lock notch 76 securely locks toggle wheel 60 against rotation to secure surgical needle 12 in arm 16. It should also be noted that depression of cam actuating lever 30 will not cause release of surgical needle 12 as release lever 84 is not in alignment with lock member 48 and thus cannot disengage and free toggle wheel 60 for rotation.

Referring now to FIGS. 13–15, to reverse the sequence, i.e. pass surgical needle from arm 16 back to arm 18, arms 16 and 18 are again moved to the closed position and continued pressure on arm 16 causes extension arm 32 to move cam actuating lever 30 through aperture 58. At this stage, at least a portion of camming surface 72 of toggle wheel 60 is located distal to center line C of cam actuating lever 30 and thus of toggle leg 86. Thus, upon depression, as cam actuating lever 30 moves through aperture 58, it again performs the dual sequential functions of causing release leg 84 to contact and disengage lock member 48 from lock notch 76 and cause toggle leg 86 to engage angled cam surface 72 and ledge 74 to initiate rotation of toggle wheel 60 in a counterclockwise direction.

Counterclockwise rotation of toggle 60 retracts needle engaging member 34 out of engagement with surgical needle 12 and advances needle engaging member 36 into engagement with surgical needle 12 in a manner similar to that described above. Knock off pin 80 also cams release leg 84 away from lock member 48 (see FIG. 15). Thus upon complete counterclockwise rotation of toggle wheel 60, lock member 48 will again engage lock notch 78 thereby securing toggle wheel 60 and locking surgical needle 12 back within recess 90 in arm 18. Arms 16 and 18 are then released to return to this open position. The apparatus, reciprocating mechanism and needle 12 are thus returned to the original position shown in FIGS. 2A and 2B. In this manner surgical needle 12 may be repeatedly and passed back and forth between arms 16 and 18 upon closure of arms 16 and 18. Thus, surgical needle 12 is under the total and precise control of an operator during an entire suturing operation without risk of needle 12 being released. It can be appreciated from the discussion above that closure of arms 18 and 16 due to pressure thereon, automatically reciprocates needle securing members 34, 36 to transfer control of surgical needle 12 to the respective arm 16 and 18. Thus, by merely squeezing arms 16 and 18 together, surgical needle 12 is automatically transferred from arm 18 to arm 16 without additional effort or manipulations on the part of the user.

FIGS. 16A through 16I illustrate the use of vascular suturing apparatus 10 to attach a pair of vascular tissue sections. The operation of apparatus 10 is best described in terms of suturing open or free ends of vessels to form an end-to-end anastomosis procedure. It will be appreciated by those skilled in the art that a similar procedure and operation of apparatus 10 is readily applicable to suture an open end of a vascular tissue section to an incision in a side of a second vascular tissue second to form an end to side anastomosis or to suture the sides of vascular tissue sections to form a side to side anastomosis.

In order to facilitate discussion of the anastomosis procedure, the operation of vascular suturing apparatus 10 will be described solely in terms of arms 16 and 18, and their respective distal ends 26 and 28 along with surgical needle 12 and associated length of suture material 14. However, it will be appreciated that the working operations of vascular suturing apparatus 10 e.g. the passing of the surgical needle 12 between arms 16 and 18, are performed in the manner described above.

FIG. 16A shows a pair of vascular tissue sections or vessels A and B. As noted above, suturing of vascular tissue sections is typically accomplished under magnification or within a reduced field of view. Thus the following operation will be described as being performed within a restricted space or field of view indicated by circular line D. Ends A1 and B1 of vascular tissue sections A and B, respectively, are prepared in known fashion to ensure that clean and undamaged tissues are sutured together.

In order to form surfaces through which surgical needle 12 can readily be inserted, ends A1 and B1 are preferably everted or spread open in known fashion to create everted edges A2 and B2 in vessels A and B, respectively, (FIG. 16B).

Vessels A and B are approximated to bring everted edges A2 and B2 into an abutting relationship as shown in FIG. 16C. At this point, vascular suturing apparatus 10 is brought within the field of view by manipulating distal ends 26 and 28 of arms 16 and 18, respectively, adjacent everted edges A2–B2. As shown, preferably surgical needle 12 and associated length of suture material 14 initially contained within arm 18 are positioned adjacent one side of everted edges A2–B2 while distal end 26 of arm 16 is positioned adjacent an opposite edge of everted edges A2–B2.

Arms 16 and 18 are closed together to insert needle 12 through everted edges A2–B2 and enter into distal end 26 on the opposite arm 16 (FIG. 16D). At this point continued operation of vascular suturing apparatus 10 causes control of surgical needle 12 to be automatically transferred from arm 18 to arm 16 in the manner described above. Additionally, as arms 16 and 18 are closed about everted edges A2–B2, spacer block 56 (described above with respect to FIGS. 1 and 2A) maintains a working gap E between arms 16 and 18 to prevent undesired compression or possible crushing of everted edges A2–B2 of vascular tissue sections A and B.

Upon opening of arms 16 and 18, (FIG. 16E) surgical needle 12 is securely held within arm 16 and is drawn through the everted edges A2–B2 of vessels A and B along with a portion of length of suture material 14. In this manner, vessels A and B have been pierced and thereby have a suture stitch formed therein.

Referring to FIG. 16F, once length of suture material 14 has been at least partially drawn through both everted edges A2–B2, length of suture material 14 may be tied off to form a single stitch in edges A2–B2.

Alternatively, arms 16 and 18 may be closed in a manner described hereinabove to repass or transfer control of surgical needle 12 from arm 16 back to arm 18 and thus reposition the point of surgical needle 12 to again pierce tissue and form another stitch. Thereafter, jaws 16 and 18 may be opened with needle 12 securely held within jaw 18 and again positioned on opposite sides of everted edges A2–B2 to form another stitch (FIG. 16G). Thus, continued repetition of the above described procedure will form a series of overlapping stitches through everted edges A2–B2 as best illustrated in FIGS. 16H and 16I.

Thus, it is possible in the above described manner to suture or pass a length of suture material through a vascular tissue section by positioning a surgical needle held within a first arm adjacent the vascular tissue section to be sutured and closing the first arm adjacent a second arm. The needle may then subsequently be transferred to the second arm and opened to draw the surgical needle and length of suture material through the tissue section. This procedure may be repeated to perform a series of stitches in a single vascular tissue section or to join two or more tissue vascular tissue sections together, for example, in side to side or end-to-end in anastomosis procedures. The above described operation occurs automatically upon closure of the arms and no further manipulation on the part of the operator are required to transfer the surgical needle from one arm to another.

While the discussion above contemplates piercing two vascular tissue sections upon a single closure of apparatus 10, it is well within the knowledge of those skilled in the art to suture vascular tissue sections by piercing a single vascular tissue section with needle 12 at a time and drawing suture material 14 therethrough. Thus, in extremely delicate procedures it is possible to insert a portion of length of suture material 14 within only a single vascular tissue at a time to suture a pair of vascular tissue sections together.

The above description of surgical suturing apparatus 10, its method of operation, and the various methods of suturing vascular tissues best illustrate the preferred embodiments and methods associated with vascular suturing apparatus 10.

However, as noted above, a double pointed surgical needle, or surgical incision member as described in U.S. patent application Ser. No. 08/260,579, filed Jun. 16. 1994, may be utilized which will allow suturing in both directions without having to repass a single pointed surgical needle and suture back to an opposing arm to form another stitch. Further, as will be appreciated by those skilled in the art, various alternate arm distal end configurations along with alternate blade or needle engaging member configurations may be provided to facilitate suturing of various vascular tissues. The following alternate arm and needle engaging member configurations and embodiments are suitable for use in vascular suturing apparatus 10 and will therefore be described merely in terms of the arm and blade interactions with surgical needle 12.

FIGS. 17A and 17B illustrate an alternate embodiment of a distal end arm configuration 110 and needle engaging member 112. Arm distal end 110 includes an enlarged bore 114 for receipt of a surgical needle 12. Bore 114 aids in positioning and transferring surgical needle 12 between arms especially when pushed through tough tissue sections which may cause deflection of surgical needle 12. Bore 114 includes a V-shaped notch 116 at a distalmost end which cooperates with a V-shaped camming edge 118 on needle engaging member 112. Thus, as shown in FIG. 17B, upon distal movement of engaging member 112, V-shaped camming edge 118 cams surgical needle 12 within bore 114 against notch 116 to securely hold surgical needle 12 therein. As noted above, surgical needle 12 may be either smooth sided or notched adjacent an edge to receive at least a portion of V-shaped camming edge 118 of needle engaging member 112.

FIGS. 18A and 18B illustrate an alternate arm 120 and blade or needle engaging member 122 configuration which utilizes proximal retraction, rather than distal advancement, of engaging member 122 to securely hold surgical needle 12 against arm 120. Arm 120 includes a V-shaped engagement notch 124 formed on the distal end while needle engaging member 122 contains an elongated slot 126 for receipt of surgical needle 12 therein. Referring to FIG. 18B, as blade 122 is retracted, surgical needle 12 disposed within slot 126 is cammed against and securely held within notch 124 in arm 120.

FIGS. 19A and 19B illustrate yet another alternate embodiment of an arm distal end 128 and needle engaging member 130 configuration best suited for securing a U-shaped, half-circle or otherwise relatively hollow surgical needle 132 which preferably has engagement structure in the form of an engagement hole 134 formed therethrough. Surgical needle 132 (FIG. 19C) may have various cross-sectional configurations while still having suitable engagement structure in the form of hole 134. Arm 128 has a bore 136 formed therein and needle engaging member 130 has a projecting tip 138 which preferably corresponds to the interior shape of the surgical needle 132. Needle engaging member 130 is further formed with a point or finger 140 formed on tip 138 and which is specifically designed to engage the engagement structure or hole 134 in surgical needle 132. Thus, upon positioning of surgical needle 132 within recess 136, distal advancement of needle engaging member 130 causes finger 140 to engage hole 134 and securely hold surgical needle 132 within arm 128.

Referring now to FIGS. 20A and 20B, an alternate arm 142 and needle engaging member 144 is shown for securely holding a round or otherwise preferably solid cross-sectional surgical needle 12 which enables easier loading. Arm 142 preferably includes an angled forward edge 146 and a groove or slot 148 proximal to angled forward edge 146. Needle engaging member 144 also includes an angled forward edge 150 and a camming member 152 formed at a distalmost portion of angled edge 150. Thus, referring to FIG. 20B, upon retraction of needle engaging member 144 camming member 152 slides past edge 146 and forces surgical needle 12 into recess slot 148, thereby securing surgical needle 12 within arm 142.

Figure 22A:
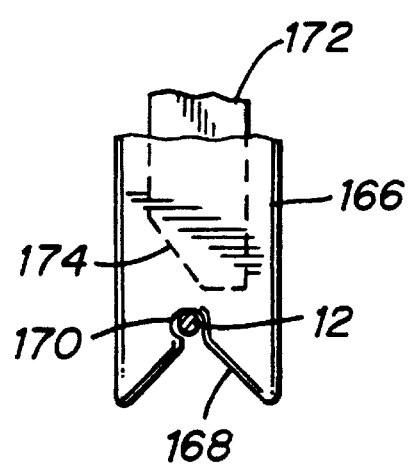
FIGS. 22A and 22B are enlarged views of another alternate distal end and needle engaging member configuration designed for easy loading of a surgical needle.
Figure 22B:
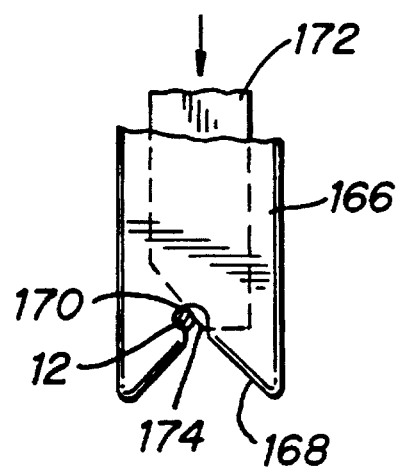

While the above described arm and needle engaging member configurations include enclosed recesses or holes through which surgical needle 12 may be perpendicularly inserted, it may often be desirable to provide open ended or easy loading structure which will allow surgical needle 12 to be inserted parallel rather than perpendicular to the arm structure. Turning first to the embodiment of FIGS. 22A, 22B, arm 166 is preferably formed with a V-shaped needle guiding recess 168 having a relatively round or circular needle receiving portion 170 at the apex of the V. Thus, advancement of arm 166 distally towards surgical needle 12 will allow needle 12 to be inserted into recess 160 from the distal end of arm 166, i.e., parallel to its longitudinal axis, rather than moving surgical needle 12 perpendicularly to arm 166 to enter an enclosed recess. Needle engaging member 172 includes an angled surface 174 which, when advanced as shown in FIG. 22B, cams against surgical needle 12 to firmly hold surgical needle 12 within circular recess 170 of arm 166. It will particularly appreciated that the easy load style of arm distal end configurations and needle engaging member configurations are particularly suited to parallel moving jaw structure which may either move perpendicular to the longitudinal axis of a surgical needle, that is, slide parallel to each other or may move parallel to the longitudinal axis of a surgical needle, i.e., that is, move perpendicular with respect to each other.

Figure 23A:
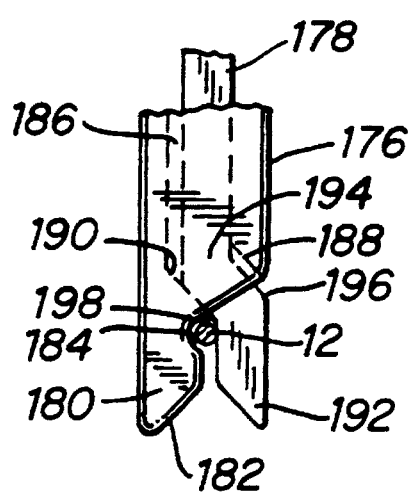
FIGS. 23A and 23B are enlarged views of an alternate easy load style distal end and needle engaging member configuration.
Figure 23B:
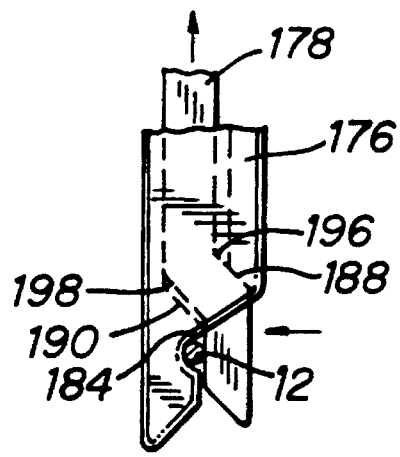

Referring now to FIGS. 23A and 23B, there is disclosed a further alternate easy load style arm distal end and needle engaging member configuration. Arm 176 preferably includes a single, distally extending hook 180 having an angled needle guiding front surface 182 and small semicircular recess 184 disposed distally of angled needle guiding front surface 182. Additionally, a channel 186 for receipt of needle engaging member 178 includes a pair of angled camming surfaces 188 and 190. Needle engaging member 178 includes a distally extending camming finger 192 having a dog leg connecting portion 194 which connects finger 192 to the remainder of needle engaging member 178. Dog leg portion 194 has camming edges 196 and 198 which cooperate with camming edges 188, 190, respectively, in arm 176. As best shown in FIG. 23B, as needle engaging member 178 is retracted, camming edge 196 abuts camming edge 188 to move finger 192 sideways forcing surgical needle 12 to be firmly held within recess 184 in arm 176. Similarly, distal advancement of needle engaging member 178 results in abutting camming edge 190 of arm 178 to engage cam edge 198 to again move finger 192 sideways away from recess 184 thereby releasing surgical needle 12 from arm 176.

Figure 24A:
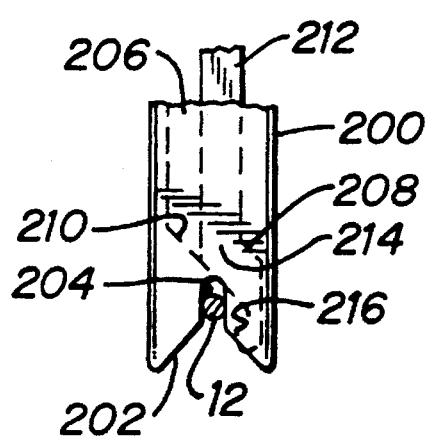
FIGS. 24A and 24B are enlarged views of still another alternate easy load style distal end and needle engaging member configuration.
Figure 24B:
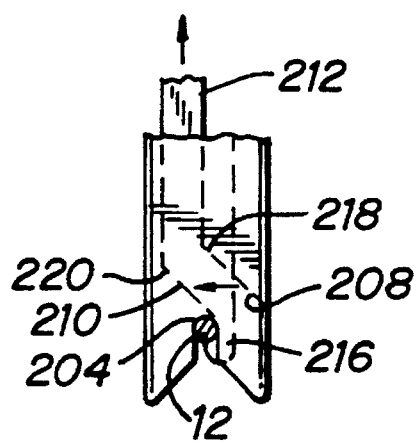

FIGS. 24A and 24B illustrate a further alternate embodiment of an easy load style arm and needle engaging member configuration. Arm 200 preferably includes a V-shaped needle guiding distal end 202 terminating in an elongated slot or recess 204 for receipt of surgical needle 12 therein. Preferably, arm 200 has an elongated needle engaging member channel 206 having angled edges 208 and 210. Needle engaging member 212 includes a dog leg end portion 214 similar to that described with respect to the embodiment disclosed in FIGS. 23A and 23B and contains a hook or recess edge 216 at the distalmost end thereof. Thus, as shown in FIG. 24B, upon proximal retraction of needle engaging member 212, a camming edge 218 on needle engaging member 212 engages angled edge 208 on arm 200 to move needle engaging member 212 sideways thereby capturing surgical needle 12 within recess 204 by curved finger or hook 216. Similarly, distal advancement of needle engaging member 212 within channel 206 causes a camming edge 220 on needle engaging member 212 to engage angled edge 210 on arm 200 to move hook 216 away from recess 204 thereby releasing surgical needle 12 from arm 200.

Figure 21:
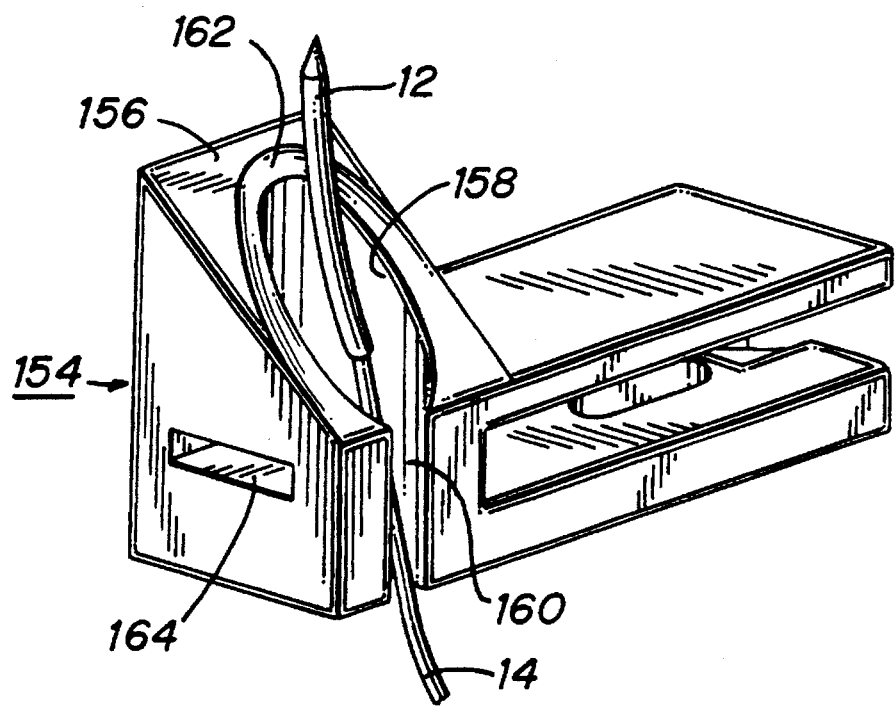
FIG. 21 is an enlarged view of an alternate suturing apparatus distal end slotted for ease in manipulation of a length of suture affixed to a surgical needle.

Referring now to FIG. 21, an arm 154 is illustrated which is particularly suited for use with a single pointed surgical needle 12 having an associated length of suture material 14 extending from an opposite end of the point. Arm 154 is configured to manage and manipulate suture material 14 such that it does not interfere with the transfer of surgical needle 12 from an opposing arm similar to arm 16. Preferably, arm 154 includes angular inwardly sloped projecting portion 156 having a recess 158 therethrough. Recess 158 has a slot 160 along one edge thereof to allow suture material 14 to pass therethrough. Additionally, projecting portion 156 is further formed with a chamfered or channeling surface 162 which serves to guide suture material 14 through slot 160 and into recess 158. In this manner, when the surgical needle 12 is passed to arm 154, the suture will be prevented from being tangled. Additionally, the channeling surface 162, by guiding the suture material through slot 160, keeps the suture out of the way of the needle engaging member extending through slot 164. By forming the slot through arm 154, a distal end of a needle engaging member may abut surgical needle 12 to hold it within recess 158 or, alternatively, a side edge of needle engaging member may cam against an edge of surgical needle 12 to hold it within recess 158.

It will be understood that various modifications may be made to the embodiments disclosed herein. For example, as noted hereinabove, parallel movement along or perpendicular to the arm axes is contemplated as well as straight and/of double pointed surgical needles such as surgical incision members. Further, other methods of grasping a surgical needle within a single arm are contemplated. Additionally, modifications within the skill of those knowledgeable in the are may be made to the camming and reciprocating mechanisms to facilitate automatic transfer of a surgical needle from one arm to another. Therefore, the above description should not be construed as limiting, but merely as exemplifications as preferred embodiments. Those skilled in the art will envision other modifications within the scope and spirit of the claims appended hereto.

What is claimed is:

1. An apparatus for suturing tissue comprising:
   a) a first arm having a first needle engaging member mounted for movement with respect to the first arm;
   b) a second arm movably mounted to the first arm and moveable between an open position spaced from the first arm to a closed position in close cooperative alignment with tile first arm:
   c) a reciprocating mechanism connected to the first needle engaging member and mounted for movement with respect to at least one of the arms, the reciprocating mechanism movable between a first position moving the first needle engaging member into engagement with a surgical needle and a second position disengaging the first needle engaging member from the surgical needle; and
   d) a cam actuating lever movably mounted to one of the first and second arms and engagable with the reciprocating mechanism such that the cam actuating lever cams the reciprocating mechanism between the first and second positions.

2. The apparatus according to claim 1 wherein, the second arm has a second needle engaging member, the reciprocating mechanism connected to the second needle engaging member for alternatively moving the first and second needle engaging members with respect to the first and second arms.

3. The apparatus according to claim 1, wherein the cam actuating lever automatically cams the reciprocating mechanism between the first and second positions in response to closure of the arms.

4. The apparatus according to claim 3, wherein the reciprocating mechanism includes a toggle wheel rotatably mounted on at least one of the first and second arms.

5. The apparatus according to claim 4, wherein a proximal end of each of the first and second needle engaging members is connected to opposite sides of the toggle wheel such that rotation of the toggle wheel simultaneously retracts one of the needle engaging members and advances the other.

6. The apparatus according to claim 4, wherein the cam actuating lever is mounted on one of the first and second arms, such that movement of the arms to the closed position drives the cam actuating lever into engagement with camming surfaces on the toggle wheel to rotate the toggle wheel.

7. The apparatus according to claim 1, further comprising a lockout member movably mounted on at least one of the first and second arms and mounted for movement between a locked position blocking movement of the reciprocating mechanism and an unlocked position disassociated from the reciprocating mechanism.

8. The apparatus according to claim 7, wherein the cam actuating lever includes a release leg, the release leg moving the lockout member from the locked position to the unlocked position upon closure of the arms.

9. The apparatus according to claim 1, further comprising a spring member mounted between the first and second arms to bias distal ends of the first and second arms into the open position.

10. The apparatus according to claim 1, wherein the first arm has a first recess for receipt of a portion of a surgical needle therein, the first needle engaging member movable adjacent the first recess to engage the surgical needle disposed therein.

11. The apparatus according to claim 10, wherein the first arm has a longitudinal channel therein for receipt of the first needle engaging member, the first channel at least partially intersecting the first recess in the first arm.

12. The apparatus of claim 1, wherein the second arm has a second needle engaging member and the reciprocating mechanism is movable between a first position advancing the first needle engaging member with respect to the first arm and a second position advancing the second needle engaging member with respect to the second arm.

13. The apparatus according to claim 12, wherein the reciprocating mechanism includes a toggle wheel rotatably affixed to at least one of the arms and having first and second camming surfaces such that an initial closure of the arms forces the cam actuating lever into engagement with the first camming surface to automatically move the toggle wheel to the first position and a subsequent closure of the arms forces the cam actuating lever into engagement with the second camming surface to automatically move the toggle wheel to the second position.

14. An apparatus for suturing vascular tissue sections comprising:

a) a pair of needle holding tweezer like arms movably interconnected at a proximal end for movement between open and closed positions; and b) a securing mechanism movably mounted with respect to the pair of arms distally of the interconnection and engagable with a surgical needle to secure the surgical needle alternately within each arm of the pair of arms in response to closure of the arms.

15. The apparatus according to claim 14, wherein the securing mechanism includes a needle engaging member slidably disposed within each arm of the pair of arms and alternately engagable with the surgical needle.

16. The apparatus according to claim 15, wherein the securing mechanism further includes a reciprocating mechanism movable for alternately advancing and retracting each of the needle engaging members in response to closure of the arms.

17. A method of suturing a pair of vascular tissue sections comprising:

a) providing a suturing apparatus having first and second needle holding members;

b) holding a surgical needle within the first needle holding member of the suturing apparatus;

c) preparing a pair of vascular tissue sections by everting ends of the vascular tissue sections to form a pair of everted edges;

d) aligning the everted ends of the vascular tissue sections and bringing the everted edges together in abutting relationship;

e) positioning the first and second needle holding members about the everted edges;

f) closing the first and second needle holding members to pierce the everted edges with the surgical needle;

g) passing the surgical needle from the first needle holding member to the second needle holding member of the suturing apparatus;

h) opening the first and second needle holding members; and i) drawing a length of suture material affixed to the surgical needle through the everted edges.

18. The method of claim 17 wherein the step of holding the surgical needle within the first needle holding member includes the steps of providing a first needle engaging member movably mounted within the first needle holding member and engaging the surgical needle with the first needle engaging member.

19. The method of claim 18 wherein the step of passing the surgical needle from the first needle holding member to the second needle holding member includes the steps of fully closing the first and second needle holding members to automatically disengage the first needle engaging member from the surgical needle and move a second needle engaging member positioned in the second needle holding member into engagement with the surgical needle.

20. The method of claim 19 wherein the step of disengaging the first needle engaging member from the surgical needle and the step of engaging the surgical needle with the second needle engaging member occur simultaneously.

21. A method of threading a suture through a vascular tissue section comprising the steps of:

a) providing an apparatus having a first tweezer like arm having a first needle receiving recess and a second tweezer like arm having a second needle receiving recess, the first and second arms pivotably connected at proximal end portions and relatively movable toward and away from each other;

b) holding a surgical needle within the first needle receiving recess;

c) positioning the first and second arms about a pair of vascular tissue sections;

d) directly compressing the first and second arms to initially move the second arm toward the first arm such that the surgical needle pierces the vascular tissue sections and enters the first needle receiving recess and subsequently releases the surgical needle from the first needle receiving recess and holds the surgical needle within the second needle receiving recess; and e) moving the first arm away from the second arm to draw a suture affixed to the surgical needle at least partially through the vascular tissue sections.

22. The method according to claim 21, further comprising the step of transferring the surgical needle from the first arm back to the second arm by recompressing the arms.

* * * * *